Figure 1:
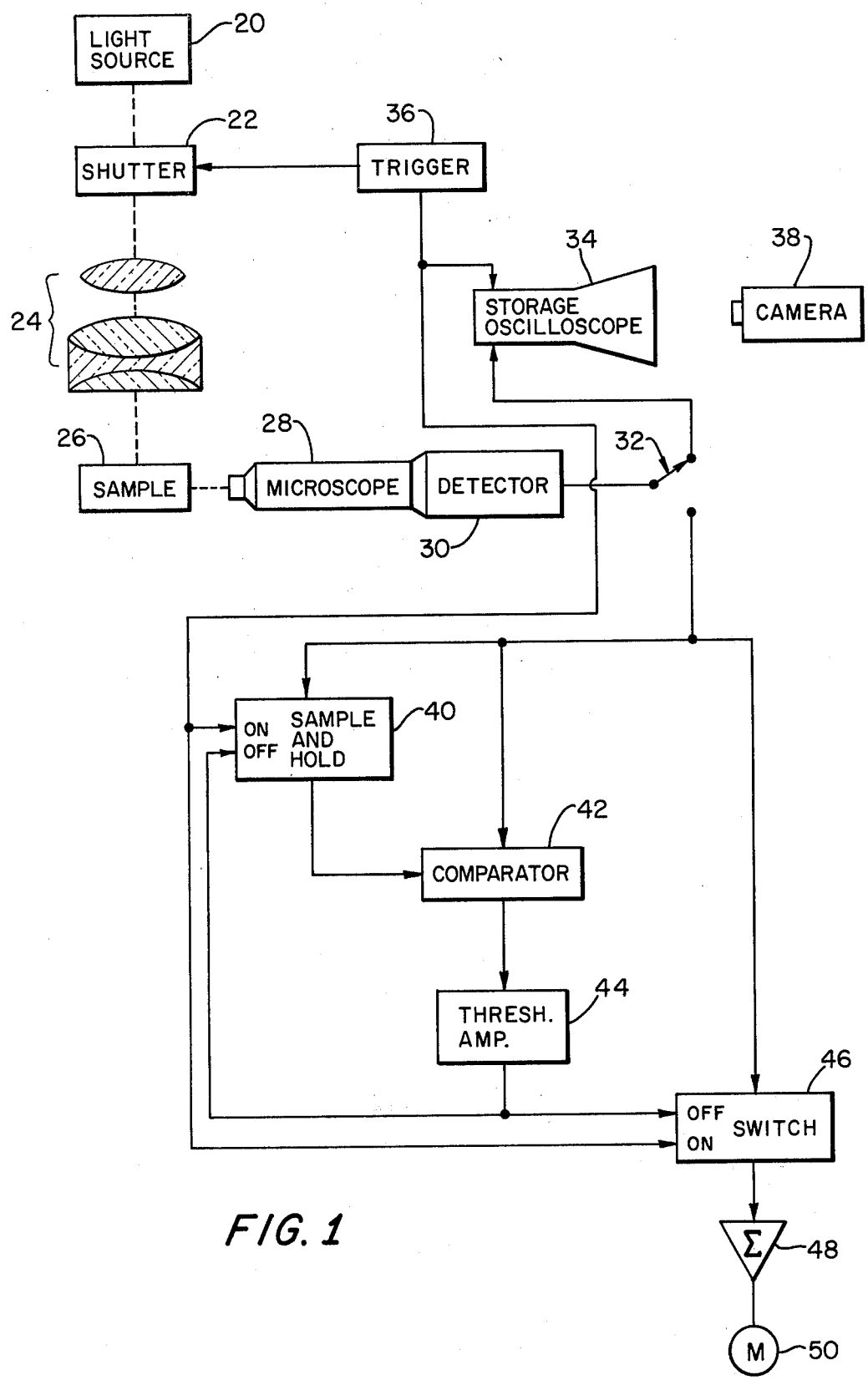

United States Patent [19]

Hirschfeld

[11] 4,018,530
[45] Apr. 19, 1977

[54] FLUORESCENCE SPECTROMETRY EMPLOYING EXCITATION OF BLEACHING INTENSITY

[75] Inventor: Tomas Hirschfeld, Framingham, Mass.

[73] Assignee: Block Engineering, Inc., Cambridge, Mass.

[22] Filed: Nov. 18, 1975

[21] Appl. No.: 633,010

[52] U.S. Cl. .............................. 356/85; 250/459; 356/98
[51] Int. Cl.[2] .......................................... G01J 3/30
[58] Field of Search ............................ 356/85, 98; 250/458–461

[56] References Cited

UNITED STATES PATENTS

| 3,829,696 | 8/1974 | Birnbaum | 250/461 |
| 3,886,363 | 5/1975 | Ohnishi et al. | 356/98 |

OTHER PUBLICATIONS

Microscope Phase Fluorometer for Determining the Fluorescence Lifetimes of Fluorochromes; Venetta; Review of Sci. Inst.; June 1959, pp. 450–451.

*Primary Examiner*—Vincent P. McGraw
*Attorney, Agent, or Firm*—Schiller & Pandiscio

[57] ABSTRACT

An improved system is desired for examining fluorescent material. The method comprises the steps of illuminating material with radiation at a fluorescent excitation wavelength of said material and at an intensity sufficient to cause bleaching of the material; detecting over a time interval commencing with initial illumination of the material, fluorescent emission produced by the material during bleaching of the latter by the radiation; and integrating over the interval the fluorescent emission detected during the bleaching of the material. Means are provided for illuminating the material to cause bleaching, for detecting fluorescent emission produced during bleaching, for measuring the decay time interval, and for integrating a signal from the detecting means over a time interval.

8 Claims, 1 Drawing Figure

FLUORESCENCE SPECTROMETRY EMPLOYING EXCITATION OF BLEACHING INTENSITY

This present invention relates to photometric systems and more particularly to such a system for examining fluorescent materials such as dyes and submicron sized histological particles stained with a fluorescent stain.

A technique commonly in use involves the use of fluorescence or luminescence spectrometry in which one or more materials, e.g., histological specimens dyed with a fluorescent stain are illuminated with radiation in the excitation wavelength of the stain so that the latter fluoresces. The parameters of the fluorescence (e.g. intensity, decay lifetime, spectral distribution, etc.) are then used to characterize the specimen. For example, observing single particles seriatim as in a number of automatic flow systems, the intensity of fluorescent emission from each particle can be proportional to the particle size, the distribution of emission can be related to the particle shape, etc. In histological spectrometry, such parameters are often useful in clinical identification.

There are however, a number of problems associated with the technique, tending to limit its applicability. First, many dyes exhibit very low intensity fluorescent emission in proportion to the intensity of the excitation radiation, and so do not appear to be suitable for use in fluorescence spectrometry. Even with high intensity fluorescing dyes, if one increases the intensity of excitation radiation, the dye bleaches generally at a rate proportional to excitation intensity, typically through photolytic decomposition. The procedures of the prior art have therefore been practically limited to dyes which exhibit high quantum efficiencies (i.e. the ratio of photons emitted by the dye molecule per the number of absorbed incident photons of excitation wavelength), and to the use of relatively low intensity excitation radiation, thereby reducing or minimizing bleaching. In many cases, to obtain enhanced fluorescence relative to the background, dyeing is accomplished with fluorochrome dyes, i.e. a dye which fluoresces with substantially greater quantum efficiency when bound to a substrate that when present as a free due molecule in solution. However, the increase in quantum efficiency for a dye may depend upon the nature of the substrate, and if absent the dye is not a fluorochrome.

Additionally, a phenomenon known as concentration quenching occurs in fluorescence spectrometry, i.e. if a high local concentration of dye exists (as when a histological particle, such as an organic molecule, has a plurality of dyed molecules bound thereto in very close proximity to one another), such multiple loading tends to reduce the quantum efficiency of the fluorescence induced in the bound dye molecules.

It is therefore the principal object of the present invention to provide a method of and apparatus for obtaining a maximum possible fluorescent signal from a particle dyed with a fluorescent stain. Another object of the present invention is to provide a system for examining minute particles dyed with one or more fluorescent stains in which the effect of a change in quantum efficiency of the fluorescent dye (for example due to concentration quenching by multiple loading) upon the fluorescent output signal or the effect of bleaching due to high levels of excitation illumination is minimized or becomes immaterial. Yet other objects of the present invention are to provide a method of examining particles which are dyed with fluorescent dyes normally not considered useful in the prior art for fluorescence spectrometry for lack of adequate quantum efficiency or fluorescent intensity and to provide a novel method of fluorescence spectrometry. Still other objects of the present invention are to provide a system of measuring the difference in quantum efficiency between two states of a fluorescent material, to provide a system for discriminating between two different quantum efficiency states of a dye, and to provide a system for measuring the concentration of a fluorescent material independent of the quantum efficiency of the dye. Other objects of the present invention will in part be obvious and will in part appear hereinafter. The invention accordingly comprises the apparatus possessing the construction, combination of elements, and arrangement of parts and the method comprising the several steps and relation and order thereof, all of which are exemplified in the following detailed disclosure, and the scope of the application of which will be indicated in the claims.

For a fuller understanding of the nature and objects of the present invention, reference should be had to the following detailed descrption taken in connection with the accompanying drawing wherein:

FIG. 1 is a block diagram of an exemplary apparatus useful in carrying out the technique of the present invention.

According to Kirchoff's equivalence relation, the fluorescence emission rate (i.e. probability of emission per dye molecule per unit time) or its reciprocal, the natural fluorescence lifetime ($\tau_F$) (i.e. the time required for the fluorescence to decay from its maximum I following cessation of excitation to a value of I/e, where e is the Naperian base) is invariant when the dye molecule is exposed to external perturbations induced for example by increases in the local concentration of the number of fluorescent molecules, unless such perturbations are strong enough to produce, in an extreme case, substantial changes in the absorption spectrum. As noted above, the effect of increases in concentration, i.e. concentration quenching, thus reduces the quantum efficiency of fluorescence without affecting the fluorescence emission rate of the mean excited molecule. One may then postulate that it is thus the lifetime ($\tau_L$) of the mean molecule in its excited state that is being reduced. In other words, the quantum efficiency drops because non-radiative processes carry away a larger fraction of the energy, and this decay mechanism will then lower the lifetime of the excited state of the molecule. The natural fluorescence lifetime ($\tau_F$) being invariant at least to the first order, the fluorescent quantum efficiency ($Q_F$) is then proportional to the lifetime of the excited state. Because quantum efficiency can be defined in this case as the ratio of the excited state lifetime to the natural fluorescence lifetime ($\tau_L/\tau_F$), $Q_F$ is then seen to be proportional to the reciprocal of the natural fluorescence lifetime.

When a fluorescent molecule is studied under very high steady state illumination (e.g. greater than 100 watts/cm$^2$ for fluorescein) such as will typically be required for extreme sensitivity work, the fluorescent molecule will be repeatedly excited at very short intervals and will spend an appreciable fraction of the time in the excited state. Under these conditions, the susceptibility of such an excited state to decomposition by photolysis or by other chemical reactions becomes very important. In other words, intense illumination tends to produce a rapidly fading fluorescent emission, or bleaching, as the molecules decompose. The total energy emitted by the excited molecules will then be a function of the initial emitted fluorescent power (determined by the number of fluorescent molecules present, the illumination intensity and the quantum efficiency of the fluorescent molecules) and of the decomposition lifetime of the molecule. Integration of this function to the point of complete bleaching shows the total emitted energy to be proportional to the product of the quantum efficiency and the decomposition lifetime. The decomposition lifetime must necessarily be inversely proportional to the fraction of the time that the molecule spends in the excited state, and this fraction of time in turn is proportional, for any given illumination intensity to the lifetime of the molecular excited state.

Thus, if we consider the proportionality of the lifetime of the mean molecule in its excited state ($\tau_L$) with the bleaching lifetime ($\tau_B$) (i.e. the amount of time required to effect substantially complete bleaching of a plurality of the dye molecules under a given illumination intensity), we note that the product of the quantum efficiency times the bleaching lifetime is a constant. Bleaching can be considered complete when output radiation or fluorescent emission is substantially non-detectable or below the noise of the detection system.

Inasmuch as the total amount or number of photons which are emitted by an excited population of a given number of particular dye molecules is a constant, if one measures the integral of the entire output fluorescence during the bleaching lifetime of the dye, one obtains thereby the maximum signal that one can possibly get from that population. Z The present invention therefore generally is a system of examining fluorescent materials such as histological particles, or the like, even of submicron size, which materials are per se fluorescent stain, and comprises the steps of first illuminating the material with radiation at an excitation wavelength at an exposure (i.e. intensity-time product) sufficient to cause bleaching. Time of exposure of material to such radiation can run from a few milliseconds to as much as a few hundred milliseconds for practical purposes but need only be a substantial fraction (i.e. > ½) of the bleaching lifetime. While the fluorescing material is exposed to the excitational illumination, the instantaneous fluorescence emission intensity from the material is detected and a measurement is made of the time interval required for the fluorescent intensity to decay during bleaching, from its initial intensity $I_o$ to some predetermined fraction of the intensity, e.g. $I_o/e$ where e is the Naperian base. The time interval thus measured is proportional to $\tau_F$ and hence $Q_F$. If desired, a value proportional to the total emission energy, typically an integral of the signal from the photoelectric detector over that time integral can be obtained. This integral is proportional to the maximum energy obtainable from the fluorescent particles.

The term "fluorescence" as used herein is intended to mean a luminescence stimulated by radiation and emitted during stimulation. The term "fluorescent stain" is intended to include fluorochrome as well as fluorescent stains or dyes, where the context so permits.

Referring now to FIG. 1 there will be shown a particle detecting system embodying the principles of the present invention and comprising light source 20 for producing a beam of coherent light. Although spatial coherence is not necessary, typically light source 20 can be a laser (such as that manufactured by Spectra Physics) which for example, provides a 10 mW output at the desired absorption wavelength of the dyed particles. Disposed in the path of the beam from light source 20 is shutter 22, preferably a standard type of electrical relay operated shutter having means defining an aperture and a blade or obturator, such as an iris, which can expose or open the shutter aperture for intervals, for example of 1/50 second with rise times in the nature of around 0.5 ms.

Disposed in the path of radiation traversing shutter 22 is an optical train 24 typically comprising a 4× objective lens followed by an achromat lens typically having 22 mm $\phi$ and a focal length of 44 mm. Optical train 24 is intended to direct light from source 22 traversing shutter 22 onto specimen holder 26. The latter is intended to support a specimen containing the particles to be examined or can be a flow cell or the like. Specimen holder 26 for example, a Beckman 1 mm quartz sample cell, is in the focal plane of the objective of microscope 28. The latter typically has a 4× objective lens preceeded with a diaphragm having a pinhole aperture of about 100 micron diameter. The microscope is also provided with a filter for blanking out (i.e. completely absorbing) the specific exciting wavelengths while preferably fully transmitting the fluorescent emissions.

Disposed at the eyepiece of microscope 28 is a photodetector such as photomultiplier tube 30, for converting the amplitude of the light seen by microscope 28 into proportional electrical signals such as voltages. The output of photomultiplier tube 30 is connectable through manual switch 32 to an output display system, here shown as a storage type cathode ray oscilloscope 34 such as Textronix Type 546B. Both the oscilloscope 34 and shutter 22 are connected to a manually operable electrical trigger 36 which when actuated provides a pulse which simultaneously initiates operation of shutter 22 so that the latter makes, for example a 1/50 second exposure, and enables oscilloscope 34 to store the signal from photomultiplier tube 30. The trace presented on the face of storage oscilloscope 34 can readily be permanently recorded, as by camera 38.

The output of photomultiplier tube 30 is also connectable through switch 32 to an electrical integrating circuit for integrating the output of detector 30 over a variable time period which is a function of the initial intensity of fluorescent radiation from sample holder 36. The electrical integrating circuit in the form shown comprises a known sample-and-hold circuit 40 connected to the output of switch 32 and also connected to trigger 36 so as to be actuated by the latter so as to sample the output of detector 30 immediately following opening of shutter 22. The electrical integrating circuit also includes known comparator 42 having one input connected to the output of detector 30 through switch 32 and another input connected to the output of sample-and-hold circuit 40. Comparator 42 is intended to provide an output signal which has an amplitude dependent on the ratio of the input signal magnitude from detector 30. The output of comparator 42 is connected as an input to known thresholding amplifier 44. The latter typically provides a signal output only when the signal at its input has risen above a certain threshold value, in this case preferably when the comparator indicates that the amplitude of the signal from circuit 40 is $e$ times the amplitude of the signal from detector 30.

The output of detector 30 is also connected through switch 32 to the input of switch 46. The output of the latter is connected to the input of integrator 48, typically an integrating operational amplifier. The output of the latter is connected to display means such as meter 50, a line printer or the like. Switch 46 is connected to the output of thresholding amplifier 44 so as to be turned "on" by a signal from the latter and is also connected to the trigger 36 so as to be turned "off" by a pulse from the latter.

The material, the examination of which is contemplated by the present invention, can be any fluorescent material or a substance or histological particle capable of having a fluorescent dye coupled therewith, whether by direct convalent chemical bonding, by coupling through an intermediate structure, by adsorption of the like. Such particles would then include, but certainly not be limited to, complex organic molecules such as enzymes, toxins, proteins, polysaccharides, lipoproteins, and the like; whole or parts of micro-organisms such as bacteria, viruses, protozoa, and the like, both live and dead; histological specimens such as cells, cell sections, mitochondria, cellular nuclei and the like; and inorganic materials such as metallic ions, ligands, molecular clusters and the like.

All tagging or dyeing of the particles is accomplished with fluorescent dye molecules, e.g. either a dye which is per se capable of fluorescent emission when excited directly by radiation in an absorption band, or a fluorochrome dye, i.e. a dye which fluoresces with a substantially greater quantum efficiency when bound to a particle than when present as a free dye molecule. Because as noted, the quantum efficiency of the dye is not a limiting factor, the present invention can make use of many dyes which have such low quantum efficiencies and therefore fluoresce so weakly, that heretofore they have not found utility in fluorescence spectrometry. Among the fluorescent dyes which are useful in the present invention are the following:

| | |
|---|---|
| Acid Violet 4BL | (C.I. No. 42575) |
| Acridine Brilliant Orange | (C.I. No. 46005) |
| Acridine Orange | (C.I. No. 46005) |
| Acridine Yellow | (C.I. No. 56025) |
| Acriflavine | (C.I. No. 46000) |
| Auramine O | (C.I. No. 41000) |
| Aurophosphine G | (C.I. No. 46035) |
| Benzo Flavine | (C.I. No. 46035) |
| Berberine Sulfate | (C.I. No. 75160) |
| Brilliant Phosphine | (C.I. No. 46035) |
| Brilliant Sulfo Flavine | (C.I. No. 56205) |
| Chrysoidine | (C.I. No. 11270) |
| Coerulein S | (C.I. No. 45510) |
| Coriphosphine O | (C.I. No. 46020) |
| Coriphosphine Fuchsin | (C.I. No. 42755) |
| Euchrysine 2G | (C.I. No. 46040) |
| Euchrysine 3 RX | (C.I. No. 46005) |
| Flavo Phosphine R. | (C.I. No. 46035) |
| Fluorescein | (C.I. No. 45350) |
| Geranine G | (C.I. No. 14930) |
| Methylene Blue | (C.I. No. 52015) |
| Morin | (C.I. No. 75660) |
| Neutral Red | (C.I. No. 50040) |
| Orange G | (C.I. No. 16230) |
| Phosphine 3R | (C.I. No. 46045) |
| Primuline | (C.I. No. 49000) |
| Pyronin GS (Pyronin extra) | (C.I. No. 45005) |
| Rhoduline Orange | (C.I. No. 46005) |
| Rhoduline Violet | (C.I. No. 29100) |
| Rosole Red B | (C.I. No. 43800) |
| Safranin | (C.I. No. 50210) |
| Scarlet R | (C.I. No. 26105) |
| Sulpho Rhodamine B | (C.I. No. 45100) |
| Tartrazine O | (C.I. No. 19140) |
| Thiazine Red R | (C.I. No. 14780) |

-continued

| | |
|---|---|
| Thiazol Yellow | (C.I. No. 19540) |
| Thioflavine S. | (C.I. No. 49010) |
| Thionin | (C.I. No. 52000) |

In many instances, the dyes will bond directly to a particle of specified nature, as well known in the art. In other instances, where the dyes will not bond or couple directly with a particular particle, or where it is desired to load a particular particle with more dye molecules than there are bonding sites, or where the multiple loading of a particle by dye molecules will cause quenching, it may be desirable to load an intermediate or carrier molecule, such as a long chain polymer, and then bond the dye-loaded polymer to the particle. Examples of molecules to which there have been covalently attached a large number of fluorescent dye molecules through a polymeric backbone are described in copending application Ser. No. 535,095, filed Dec. 20, 1974. Particularly, the latter patent application describes an antibody having coupled thereto a polymeric chain having in turn a multiplicity of fluorescent molecules coupled to the chain, without substantially impairing the specificity of the antibody. Typically, intermediates or carriers are polymeric molecules having reactive sites dispersed along the length of the chain, with a chemically different reactive site at the end of the chain. Such carrier or intermediate molecules typically can comprise polyethyleneimines, for example of molecular weight in the range of 1200–60,000; polypeptides such as polylysines; polyamides, such as nylon 6; polymeric carboxylic acids; and the like. A technique for dyeing such carriers and for coupling them to particles is described in said patent application Ser. 535,095. As earlier noted, the invention permits the use of fluorescence spectrometry of weakly fluorescent dyes such as but not limited to erythrosin, fluorochrome dyes not bound to a sensitizing substrate, quenched dyes, antifluorochrome dyes and the like.

In operation of the apparatus of FIG. 1, samples of suitable dyed particles are exposed to radiation of bleaching intensities and the intensity of the resultant fluorescent signal detected and monitored over a variable time period established from initial emission to a time when the intensity has decayed to a predetermined fraction of its original value. For example, the signal is displayed and observed on oscilloscope 34 along a horizontal time axis appropriately time calibrated. The initial intensity is observed and then the intensity after a limited period of time is observed. From the intensity increment of decay and the time required for that decay increment to occur, the bleaching lifetime $\tau_B$ (arbitrarily established as the time required for the initial intensity I to decay to I/$e$) can be readily deduced, although the bleaching lifetime of course can also be defined, If one wishes, as any multiple or submultiple of I/$e$ recognized by those skilled in the art.

To integrate total emission during $\tau_B$, assuming that the oscilloscope trace is long enough, the point on the time axis at which the initial intensity $I_o$ has fallen to I/$e$ (i.e. $I_t$) is determined and the area under the curve between Io and $I_t$, is then measured. It will also be recognized that the integral of the decay curve is the mirror image of the latter so that the integral can either be directly measured or can readily be computed from the decay curve.

If the oscilloscope trace is too short, then one may use the well-known decay equation (valid for single decay mode only):

$$I_t = I_o e^{-K\,t}$$

(where $I_o$ = initial intensity at a starting time $t_o$
  $I_t$ = intensity after some later time $t_t$
  $\Delta t = t_t - t_o$
  $K = 1/\tau$
  $e$ = the Naperian base, and
  $\tau$ = bleaching lifetime)

By measuring $I_o$, $I_t$ and $t$ one can solve for K and hence the value of $\tau$.

Alternatively, automatic integration is achieved as follows. Switch 32 is closed to connect sample-and-hold circuit 40 to the output of detector 30. Immediately after trigger 36 is activated to open shutter 22, sample-and-hold circuit 40 is enabled to read the output voltage from detector 30. If desirable, a time increment can be introduced between opening of shutter 22 and enablement of sample-and-hold circuit 40 by introduction of an appropriately timed delay line into the input to circuit 40. Circuit 40 thus samples the initial and maximum amplitude $I_m$ of the voltage output from detector 30 and holds that voltage at one input of comparator 42 at a substantially constant level. The voltage at the other input to comparator 40 is the time decaying voltage $I_t$ from detector 30. Hence, the output of comparator is proportional to the ratio $I_m/I_t$ and when $I_t$ has decayed so that the ratio reaches an arbitrary value (for example here the value e), thresholding amplifier 44 is actuated to produce an output pulse.

The activation of trigger 36 also closes switch 46 to connect the output of detector 30 to integrating amplifier 48, and the output pulse from amplifier 44 opens switch 46, terminating the integration (and also clearing circuit 40). Hence it will be seen that the integration performed by amplifier 48 is over a time period which is variable in accordance with the initial amplitude of the fluorescence seen by detector 30. The integral obtained can be displayed or otherwise further processed in meter 50.

Operation of the system of FIG. 1 to establish relative independence of signal from quantum efficiency is described in the following examples, in each of which the sample containing the dyed particles is irradiated in an absorption band of the dye by light source 20 and the fluorescence from the continuously irradiated sample is detected at one or more peak emission wavelengths by photomultiplier 30 which converts the input light intensity to a corresponding voltage. The output of photomultiplier 30, as noted, can either be stored and displayed as a continuous trace of intensity against time on oscilloscope 32 for a bleaching lifetime computed from the oscilloscope data and th desired integral then determined, or can be directly integrated over a bleaching lifetime which is automatically determined.

EXAMPLE I

Polyethyleneimine molecules are dyed with fluorescein as follows:

The fluorescein can be functionalized by the known technique of nitrating with $HNO_3$ and reducing the nitrate with nascent hydrogen produced by adding HCl and Zn, thiophosgene being then added to form fluorescein isothiocyanate. However, fluorescein isothiocyanate is also available commercially.

To an aqueous solution of 2 mg of polyethyleneimine (PEI) (mol. wt. 20,000) in 1 ml. of 0.1M sodium cacodylate at pH 7.0 is added 50 mg. of fluorescein isothiocyanate in 1.5 ml. of water. The mixture is stirred continuously for about 16 hours during which time light is excluded. Excess dye is them removed by passage through a Sephadex G-25 (silica gel) column (0.9 × 30 cm) and subsequent elution of the column with 0.1 M, pH 7.0 aqueous sodium cacodylate.

The resulting polymer/dye complex can be analyzed by the Folin-Ciocaulteau protein assay. That assay gives a linear curve with polyethylenimine and thus is suitable for estimation of the amount of polymer present. The extinction coefficient of fluorescein isothiocyanate at 495 nm. is $73 \times 10^3$ and drops to 75% of this value on binding. By measuring both polymer and dye present in a given sample of the complex, the degree of dye binding is estimated. This degree of binding depends upon the dye concentration in the initial reaction mixture. The complex prepared by the process of this Example contains approximately 80 dye molecules per molecule of PEI.

Assuming the quantum efficiency of a pure fluoresceine solution at a concentration of 5 ppm to be 100%, absorption measurement at 524 $\mu$ established that the quantum efficiency of the dyed polymer of this example was 1.79%. The product of quantum efficiency times bleaching time is therefore 145.

The dyed polymer solution was diluted with pure water to a 20× dilution and a sample placed in a 1 mm Beckman quartz sample cell 26. The sample was illuminated by laser 20 with an excitation wavelength of 4880 A and at an illumination intensity of $1.24 \times 10^4$ w/cm$^2$, fluorescence at th peak emission wavelength of 524 $\mu$ was detected by photomultiplier tube 30 and appeared on scope 34 as a 60 mv value. After 33 msec, the fluorescent intensity at 524 $\mu$ appeared on the scope to be 40 mv. The bleaching lifetime was then computed as 81.4 msec. allowing about 0.25 msec as a correction for operation of the shutter 22.

EXAMPLE II

The procedure of Example I is followed however altering the molar ratio of dye to polyethylenimine (mol. wt. 20,000) so as to provide a polymer/dye complex containing approximately 100 molecules of dye per molecule of polyethylenimine.

Upon bleaching, the resulting data yielded a corrected bleaching lifetime of 117.4 msec. The quantum efficiency of the dyed PEI in this example was measured by absorption as 13.2%, a value consistent with the increased dye loading compared to Example I. The product of quantum efficiency times bleaching time is 155, indicating substantial equivalence (deviation less than 7%) between the bleaching lifetime times quantum efficiency product and thus a first order independence from quantum efficiency.

EXAMPLE III

The polymer/dye complex of Example I was coupled to a commercially obtained sample of Echo 12 antibody according to the procedure described in the above-mentioned U.S. Pat. application Ser. No. 535,095 in which the PEI is first treated with glutaraldehyde (25% aqueous) buffered to pH 7.0 prior to dyeing, the polymer/dye complex then being directly reacted with the antibody. The polymer/dye antibody complex in which the antibodies have coupled thereto dye-bearing polymer molecules, was illuminated according to Example I and the resulting data provide a bleaching lifetime of 49.5 msec and a quantum efficiency of 2.03%, the product of these two values being 101.

EXAMPLE IV

The polymer/dye complex of Example II was coupled to a sample of the same Echo 12 antibody according to Example III and the resulting complex illuminated as in Example III to yield data providing a bleaching lifetime of 88.9 msec and a $Q_F$ of 1.21%. The lifetime × $Q_F$ product is 108 again exhibiting the first order independence of the technique of the invention with regard to $Q_F$.

EXAMPLE V

Polyethyleneimine of mol. wt. 1200 (5% by weight in water) was dyed with fluorescein according to Example I and samples of the dyed polymer were diluted to provide several different concentrations. Each was illuminated and the fluorescent output integrated according to Example I with the following results:

| SAMPLE CONC. | $Q_F$ | BLEACH. TIME | $Q_F$ BLEACH TIME |
|---|---|---|---|
| 100 | 93.7% | 3.0 msec | 281 |
| 333 ppm | 86.0% | 2.9 msec | 249 |
| 1000 ppm | 64.9% | 4.0 msec | 260 |
| 3330 ppm | 30.2% | 13.7 msec | 414 |

The departures from constancy of the last column, which show a surprising signal increase at low quantum efficiencies, arise from the departures from exponentiality towards the latter part of the decay curve. A reduction in the decay rate in this very small region is to be expected due to diffusion from the surroundings. That this is the cause for the above mentioned unexpected improvements is borne out by the lower intensity of the change for the samples of Examples I and II on the one hand and Examples III and IV on the other, with their much lower diffusivity. This is consistent with the mean Brownian displacement in 10 msec, which is about $0.7\mu$ for the fluorescein and about $0.3\mu$ for the polymer. Equivalence between the products of decay time times quantum efficiency of the samples of Example V with those of the other Examples is not to be expected, as they correspond to different chemical states of the dye molecule.

The first order independence from quantum efficiency of the last column, to which the received signal per molecule will be proportional, is clearly underscored. The total received signal will be proportional to the produce of this number and the loading.

As noted earlier, the principles of the present invention provide a method for determining the difference in quantum efficiency between two states of a fluorescent material. For example, it is often desirable to determine the difference in the changing quantum efficiency between the bound and unbound state of a cluorochrome dye in order to determine how effective the dye really is as a fluorescent source. The determination of the difference is quantum efficiency using the principles of the present invention is quite simple. One simply illuminates a first sample of the fluorescent material in a first state as hereinbefore described to effect bleaching, and detects the instantaneous fluorescent emission produced during the bleaching process. A measurement is made of the time interval required for the fluorescent emission from the illuminated sample to decay for example to $1/e$ times the initial intensity.

Exactly the same procedure is then followed with respect to a sample of the material in another state, the concentration and size of the two samples, assuming them to be solutions, being substantially identical with respect to the fluorescent material.

Because the bleaching lifetime $\tau$ is equal to the product of a constant K times the $Q_f$, it will be seen that the ratio of the two decay lifetimes $\tau /\tau$ is independent of the value of K and is therefore a proportional measure of the ratio of quantum efficiencies of the two states of the fluorescent material.

The foregoing can be immediately appreciated from the table in Example 5 in which it will be seen that, at least for the first three concentrations of dyed polyethyleneimine, the bleaching lifetimes are inversely proportional to the quantum efficiency. Hence, for example, the ratio, 3/4, of bleaching lifetimes of the first and third samples in Example 5 are very close to the inverse ratio of quantum efficiencies of those two samples.

The principles of the present invention can also be employed for example to determine an unknown concentration of known fluorescent materials in solution. This can be determined in accordance with the following considerations:

It will be remembered that the total fluorescent emission from each molecule of a given species is an invariant, being proportional to the ratio of the decomposition lifetime of the molecule to the natrual fluorescent lifetime of the molecule. Thus, one simply measures out a known mass of fluorescent material and dissolves it in a small volume of solvent to provide a calibration sample. The entire mass of fluorescent material is then illuminated with radiation of bleaching exposure and at a fluorescent excitation wavelength with respect to the fluorescent material. The resulting fluorescent emission is detected and summed or integrated until its initial intensity has decayed to some value, such as $I_o/e$. The integral obtained will be invariant for that amount of fluorescent material. One now illuminates a sample volume of a solution containing an unknown amount of the fluorescent material with a bleaching exposure at the same excitation radiation wavelengths, and detects and integrates the fluorescent emission until the output level drops to $I_o/e$. The ratio of the second integral to the first integral will be equal to the ratio of the unknown amount of fluorescent material in the test solution to the known amount of fluorescent material in the calibration sample. Obviously, measurement of the volume of the test solution will provide the data necessary to obtain the concentration of fluorescent material in that solution.

The principles of the present invention can also be employed, in some cases to detect and examine a fluorescent material in a mixture of fluorescent materials; for examples, a dye in a mixture of dyes in solution. Where a mixture of two dyes, for example, is of two states of the same fluorochrome dye, or is a mixed solution of two fluorescent materials of different quantum efficiencies but substantially identical emission band wavelengths, the concurrent fluorescent decay of the two will be seen to be a summation of exponential functions. The emissions curve is therefore too complex to be described and analyzed by the simple decay equation above delineated.

However, in accordance with the present invention, because the quantum efficiencies of the two materials are different, one need expose the mixture to radiation sufficient to bleach substantially only that material with the higher quantum efficiency. Fluorescence thereafter excited in and observed from the mixture will arise substantially only from the fluorescent material having the weaker quantum efficiency. This technique then permits one to separate the two materials, and if desired, to reconstruct their individual decay characteristics.

Since certain changes may be made in the above apparatus and method without departing from the scope of the invention herein involved, it is intended that all material contained in the above description or shown in the accompanying drawing shall be interpreted in an illustrative and not in a limiting sense.

What is claimed is:

1. Method of examining fluorescent material, said method comprising the steps of
   illuminating said material with radiation at a fluorescent excitation wavelength of said material and at an exposure sufficient to cause bleaching of said material;
   detecting over a time interval commencing with initial illumination of said material, fluorescent emission produced by said material during bleaching of the latter by said radiation; and
   integrating over said interval the fluorescent emission detected during the bleaching of said material.

2. Method as defined in claim 1 wherein said interval is substantially the time required for the initial intensity of said fluorescent emission has decayed to a value of about l/e times the initial intensity, where e is the natural logarithmic base.

3. Method of determining the difference in quantum efficiency between two fluorescent dyes in a mixture, said method comprising the steps of:
   illuminating a sample of said mixture with radiation at an excitation wavelength of said first dye and at an exposure sufficient to cause bleaching of said first dye;
   detecting over a time interval commencing with initial illumination of said first dye, fluorescent emission produced by bleaching of said first dye by said radiation;
   measuring the time interval required for the initial intensity of fluorescent emission from the illuminated first dye to decay, to some predetermined fraction thereof;
   illuminating said sample of said mixture with radiation at an excitation wavelength of said second dye and at an exposure sufficient to cause bleaching of said second dye;
   detecting over a time interval commencing with initial illumination of said second dye, fluorescent emission produced by bleaching of said second dye by said radiation;
   measuring the time interval required for the initial intensity of fluorescent emission from the illuminated second dye to decay to said predetermined fraction thereof; and
   comparing said time intervals required for the initial intensities of fluorescent emission from said dyes to decay.

4. Method as defined in claim 3 wherein said two dyes are different states of a fluorochrome dye and said states are respectively a bound state wherein said fluorochrome dye is bound to a selected substrate material and an unbound state wherein said fluorochrome dye is free of binding to said material.

5. Method as defined in claim 1 wherein said step of integrating is continued until the intensity of said fluorescent emission has decayed to a predetermined level to thereby obtain an integrated value, said method including the step of then obtaining a ratio between the initial instantaneous intensity of said emission and said integrated value.

6. Method of determining the amount of fluorescent material in sample solution, said method comprising the steps of:
   illuminating a known amount of said material with radiation at a fluorescent excitation wavelength of said material and at an exposure sufficient to cause bleaching of said known amount of material;
   detecting over a time interval commencing with initial illumination of said known amount of material, the fluorescent emission intensity produced by said known amount material during bleaching of the latter by said radiation, until said fluorescent emission has decayed to a predetermined fraction of its initial intensity;
   integrating over said interval the fluorescent emission detected during the bleaching of said known amount of material ot obtain a first integral;
   illuminating said sample solution with radiation at said excitation wavelength and at an exposure sufficient to cause bleaching of the material in said solution;
   detecting over a second time interval commencing with initial illumination of said solution, fluorescent emission produced by said material in said solution during bleaching of the latter by said radiation, until said emission from said material in said solution has decayed to a predetermined fraction of its initial intensity;
   integrating over said second ingterval the fluorescent emission detected during the bleaching of said material in said solution, to obtain a second integral; and
   comparing said first and second integrals.

7. Method as defined in claim 6 wherein said intervals are substantially the time required for the intitial intensity of fluorescent emission to decay a value of about 1/e times the initial intensity, where e is the natural logarithmic base.

8. Method of examining a mixture of two fluorescent materials in solution, which materials exhibit substantially similar fluorescent emission band wavelengths and have different quantum efficiencies, said method comprising the steps of
   illuminating said mixture with radiation at excitation wavelengths of said materials and with an exposure sufficient to substantially completely bleach said fluorescent material having the higher quantum efficiency, but not enough to bleach said fluorescent material having the lower quantum efficiency;
   thereafter exposing said mixture to radiation at said excitation wavelength to excite into fluorescent emission said fluorescent material having the lower quantum efficiency; and
   detecting the fluorescent emission from substantially only said fluorescent material having the lower quantum efficiency.

* * * * *